United States Patent
Dietz (10) Patent No.: US 11,109,787 B2
(45) Date of Patent: Sep. 7, 2021

(54) MULTI-TIP PROBE FOR OBTAINING BIOELECTRICAL MEASUREMENTS

(71) Applicant: Vine Medical LLC, Saint George, UT (US)

(72) Inventor: Phillip W. Dietz, Saint George, UT (US)

(73) Assignee: Vine Medical LLC, Saint George, UT (US)

( * ) Notice: Subject to any disclaimer, the term of this patent is extended or adjusted under 35 U.S.C. 154(b) by 355 days.

(21) Appl. No.: 15/985,378

(22) Filed: May 21, 2018

(65) Prior Publication Data
US 2019/0350475 A1 Nov. 21, 2019

(51) Int. Cl.
*A61B 5/00* (2006.01)
*A61B 5/25* (2021.01)
*A61B 5/291* (2021.01)

(52) U.S. Cl.
CPC .............. *A61B 5/25* (2021.01); *A61B 5/291* (2021.01); *A61H 2201/0153* (2013.01)

(58) Field of Classification Search
CPC .............. A61B 18/00875; A61B 18/14; A61B 2018/00642; A61B 2018/1467; A61B 5/25; A61B 5/291; A61B 5/0532; A61N 1/0546; A61N 1/0456; A61N 1/36021; A61N 1/36034; A61N 1/36071; A61N 1/0484; A61N 1/36; A61N 1/08; A61N 1/04; A61M 1/0025; A61H 2201/0153
USPC ................. 600/300, 372, 547, 548; 607/115
See application file for complete search history.

(56) References Cited

U.S. PATENT DOCUMENTS

| | | | |
|---|---|---|---|
| 5,215,088 A * | 6/1993 | Normann | A61B 5/04001 600/377 |
| 5,421,344 A | 6/1995 | Popp | |
| 6,928,315 B1 | 8/2005 | Nachaliel | |
| 7,131,969 B1 * | 11/2006 | Hovda | A61B 18/148 606/45 |
| 8,437,845 B2 | 5/2013 | Sarfaty et al. | |
| 9,526,432 B2 | 12/2016 | Dietz | |
| 2002/0123694 A1 * | 9/2002 | Organ | A61B 5/0536 600/547 |

(Continued)

FOREIGN PATENT DOCUMENTS

WO 2017074378 A1 5/2017

OTHER PUBLICATIONS

United States Patent and Trademark Office, "International Search Report", dated Aug. 7, 2019, International Application No. PCT/US2019/31117.

*Primary Examiner* — May A Abouelela
(74) *Attorney, Agent, or Firm* — Terrence J. Edwards; TechLaw Ventures, PLLC (57) ABSTRACT

A device for obtaining an electrical conductance reading from a patient includes a sensor head for contacting a patient's skin. The device includes a primary conductive tip positioned on the sensor head and an ancillary conductive tip positioned on the sensor head to contact a different portion of the patient's skin than the primary conductive tip. The primary conductive tip and the ancillary conductive tip are electrically isolated from each other. The primary conductive tip and the ancillary conductive tip are configured to contact a patient's skin when the sensor head is placed against the patient's skin to obtain independent measurements of electrical conductance.

13 Claims, 9 Drawing Sheets

(56) References Cited

U.S. PATENT DOCUMENTS

| | | | |
|---|---|---|---|
| 2003/0088189 A1* | 5/2003 | Tu | A61B 5/4381 600/549 |
| 2004/0054393 A1* | 3/2004 | Stemme | A61B 5/0408 600/372 |
| 2004/0092839 A1 | 5/2004 | Shin et al. | |
| 2004/0152997 A1* | 8/2004 | Davies | A61B 5/04002 600/547 |
| 2005/0065418 A1* | 3/2005 | Ginor | A61B 5/4312 600/345 |
| 2005/0085869 A1* | 4/2005 | Tehrani | A61N 1/3601 607/42 |
| 2007/0067007 A1* | 3/2007 | Schulman | A61N 1/0526 607/115 |
| 2007/0276286 A1* | 11/2007 | Miller | A61B 5/053 600/564 |
| 2009/0024052 A1* | 1/2009 | Brown | A61B 5/053 600/547 |
| 2009/0054908 A1* | 2/2009 | Zand | A61B 34/30 606/130 |
| 2009/0082702 A1 | 3/2009 | Folkerts et al. | |
| 2009/0253968 A1* | 10/2009 | Cho | A61B 5/0537 600/301 |
| 2009/0306535 A1* | 12/2009 | Davies | A61B 5/053 600/547 |
| 2010/0106047 A1* | 4/2010 | Sarfaty | A61B 5/418 600/547 |
| 2010/0217148 A1* | 8/2010 | Binder | A61B 5/4312 600/547 |
| 2010/0292603 A1* | 11/2010 | Shiftman | A61B 5/0492 600/547 |
| 2011/0082383 A1* | 4/2011 | Cory | A61B 5/0536 600/547 |
| 2011/0313311 A1* | 12/2011 | Gaw | A61B 5/0536 600/547 |
| 2012/0101552 A1* | 4/2012 | Lazarewicz | A61B 5/0484 607/62 |
| 2012/0116242 A1* | 5/2012 | Mahajan | A61B 5/055 600/547 |
| 2012/0138335 A1* | 6/2012 | Tathireddy | A61N 1/0529 174/250 |
| 2012/0245436 A1* | 9/2012 | Rutkove | A61B 5/053 600/301 |
| 2013/0261491 A1* | 10/2013 | Paul | A61B 5/015 600/547 |
| 2014/0276192 A1* | 9/2014 | Stivoric | A61B 5/4866 600/547 |
| 2015/0141767 A1* | 5/2015 | Rogers | A61B 5/015 600/301 |
| 2015/0289929 A1* | 10/2015 | Toth | A61B 5/6858 600/372 |
| 2016/0101282 A1* | 4/2016 | Bergelin | A61N 1/0496 600/547 |
| 2016/0174859 A1* | 6/2016 | Oudenhoven | A61B 5/0478 600/383 |
| 2016/0174869 A1 | 6/2016 | Park | |
| 2018/0000533 A1* | 1/2018 | Boll | A61B 18/1206 |

* cited by examiner

MULTI-TIP PROBE FOR OBTAINING BIOELECTRICAL MEASUREMENTS

TECHNICAL FIELD

The present disclosure relates bioelectrical measurements and more particularly relates to multi-tip probes for obtaining bioelectrical measurements.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

The disclosure extends to devices, methods and systems for obtaining an electrical conductance reading from a patient. The device and systems disclosed may include a sensor head for contacting a patient's skin. The device and system disclosed may also include a primary conductive tip positioned on the sensor head and an ancillary conductive tip positioned on the sensor head to contact a different portion of the patient's skin than the primary conductive tip. The primary conductive tip and the ancillary conductive tip are electrically isolated from each other. The primary conductive tip and the ancillary conductive tip are configured to contact a patient's skin when the sensor head is placed against the patient's skin to obtain independent measurements of electrical conductance. In the following description of the disclosure, reference is made to the accompanying drawings, which form a part hereof, and in which is shown by way of illustration specific implementations in which the disclosure is may be practiced. It is understood that other implementations may be utilized and structural changes may be made without departing from the scope of the disclosure.

Traditional medical science has long recognized certain electrical characteristics of humans and other living organisms. For example, the traditional medical community has recognized the electrical potentials generated by the human body in such forms as brain waves as detected by electroencephalographs (EEG), electrical impulses resulting from muscular heart activity as detected by electrocardiograms (EKG), and other electrical potentials measurable at other areas of the human body. While the relative levels of the electrical activity exhibit relatively small levels, such signals are nonetheless measurable and consistent.

In addition to measurable voltage levels, the human body and other mammalian organisms exhibit specific locations wherein the conductance values are relatively predictable for healthy individuals. The locations of anatomical dermal conductance points exhibit unique conductance values. Studies have indicated that many conductance points correspond to nerve innervations and trigger points. The conductance points are located under the skin (epidermis) and are accessed electrically through the skin either by the use of needles or by using a probe tip pressed against the skin. As the outermost layer of epidermis (cornified layer) is less conductive, the probe tip may or may not need a fluid such as water or a type of electrode gel to enhance conductivity through the epidermis to the conductance point.

Interestingly, many of these conductance points match up with traditional acupuncture points. The representative conductance points and their relationship with organs and life systems of the human body have been characterized into more than 800 points that are organized into approximately 14 basic groups or meridians. The measurable state of these conductance points reflects the condition of the related meridians and therefore the health of organs and other functions of the human body. The conductance value of normal healthy tissue at a conductance point for different individuals is generally in the same range. In at least some cases, when such tissue is inflamed or infected, the conductivity is higher such that the measured conductance value appears lower than the normal range. Additionally, if the tissue is in a degenerative state, the conductivity may be lower.

Systems have been implemented to read or measure the conductance value at these conductance points and present conductance values to a clinician for use in diagnosing a condition. However, Applicants have recognized that the traditional systems have proven difficult to use since the precise location of the points is difficult to locate and pinpoint. Furthermore, the differences in the characteristics of each patient and each point of a given patient can cause a technician to obtain inaccurate and/or unrepeatable readings. Moreover, current technologies have caused discomfort to a patient due to the number of times that a practitioner must take a conductance reading to zero in on the correct location of the conductance point.

In some cases, even upon obtaining a good measurement at the right location, it can be difficult to determine whether the measurement was good. In some systems, a first device is used to locate the points and a second device is brought in contact with the point to perform the conductance testing. While this technique is available, employing multiple devices introduces a potential for clinical error and is very time consuming. In addition, in every case the system used proves difficult to locate the conductance points on the patient. The conductance testing may sometimes be compromised when the system does not accurately determine the points. Also, repeated testing of a certain point may cause the electrical potential of the point to be compromised.

Thus, Applicants have recognized that challenges exist in the form of inaccurate readings, unrepeatable readings, pain, discomfort, examination time, and the like. Accordingly, it would be an improvement in the art to augment or even replace current devices and techniques. In light of the foregoing, the present disclosure relates to obtaining bioelectric reading or information. In one embodiment, devices and methods for an enhanced multi-surface tip are disclosed to facilitate locating and obtaining a bioelectric reading from a patient for assessment, therapeutic, and/or diagnostic purposes. According to one embodiment, device for obtaining an electrical conductance reading from a patient includes a sensor head for contacting a patient's skin. A primary conductive tip is positioned on the sensor head and an ancillary conductive tip is positioned on the sensor head to contact a different portion of the patient's skin than the primary conductive tip. The primary conductive tip and the ancillary conductive tip are electrically isolated from each other and the primary conductive tip and the ancillary conductive tip are configured to contact a patient's skin when the sensor head is placed against the patient's skin to obtain independent measurements of electrical conductance. These measurements may be taken simultaneously or sequentially.

In at least one implementation, a multi-tip sensor or sensor head is used to obtain a bioelectric reading from a patient. Each tip provides independent feedback and can be used for obtaining a bioelectric conductance reading from the patient. For example, the primary tip may include a center tip and one or more ancillary tips may be positioned around a perimeter of the center tip. If the center tip has the highest bioelectric reading (i.e., lowest resistance) or shares the highest bioelectric reading along with one or more of the ancillary tips, the reading is recorded and the sensor head is removed from the patient. However, if an ancillary tip located on an edge of the sensor head has the highest bioelectric conductance reading, the sensor head may be repositioned on the patient such that the center tip is then located in the area that had the highest bioelectric conductance reading. Then a control unit may use the sensor head to obtain new readings. This process of positioning or repositioning the sensor head and obtaining readings may be repeated until the center tip has the highest bioelectric conductance reading and is recorded. However, if the control unit determines the primary tip and one or more ancillary tips are not on a conductive point of the patient, then the control unit will provide an indication, such as a visual or audio indication, to a user that there is no bioelectric reading.

In accordance with embodiments of the present disclosure, a patient's condition may be assessed and/or diagnosed using the devices, systems, or methods disclosed herein. A multi tip sensor head or sensor head may be used to measure impedance or conductance between the location of the sensor head and a grounded location on the user's body (such as a hand). For example, the conductance measurement is obtained between the sensor head and a ground bar and may be displayed on a display or a display screen, stored in memory, or provided to other output for evaluation by a clinician or practitioner. If the conductance value at a particular conductance point on the patient is higher or lower than normal, the clinician may investigate the biological system meridian that corresponds to that conductance point. Conversely, when a particular conductance point displays a normal reading, the clinician thereafter measures the conductance at various other conductance points to properly assess and/or diagnose the condition of the patient.

Upon evaluating the condition of the patient, such as an organ disorder or a biological system abnormality, the clinician is then able to recommend a possible treatment or remedy for such a condition. These and other features and advantages of the present disclosure will be set forth or will become more fully apparent in the description that follows and in the appended claims. Those skilled in the art will appreciate that the methods and processes can be used in association with a variety of different bioelectric sensing devices, including patches, clips, and the like to provide an enhanced bioelectric sensing surface. Furthermore, the features and advantages of the disclosure may be learned by the practice of the disclosure or will be obvious from the description, as set forth hereinafter.

A detailed description of systems and methods consistent with embodiments of the present disclosure is provided below. While several embodiments are described, it should be understood that this disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments may be practiced without some or all of these details. Moreover, for the purpose of clarity, certain technical material that is known in the related art has not been described in detail in order to avoid unnecessarily obscuring the disclosure.

In the following detailed description, certain terminology is used for the purpose of reference only, and is not intended to be limiting. Terms such as "upper", "lower", "above", and "below," refer to directions in the drawings to which reference is made. Terms such as "inwards" and "outward" refer to directions towards and away from, respectively, the geometric center of the component described. Terms such as "side", "top", "bottom," "horizontal," "with in," "inside," and "vertical," describe the orientation of portions of the component within a consistent but arbitrary frame of reference which is made clear by reference to the text and the associated drawings describing the component under discussion. Such terminology includes words specifically mentioned above, derivatives thereof, and words of similar import.

Figure 1:
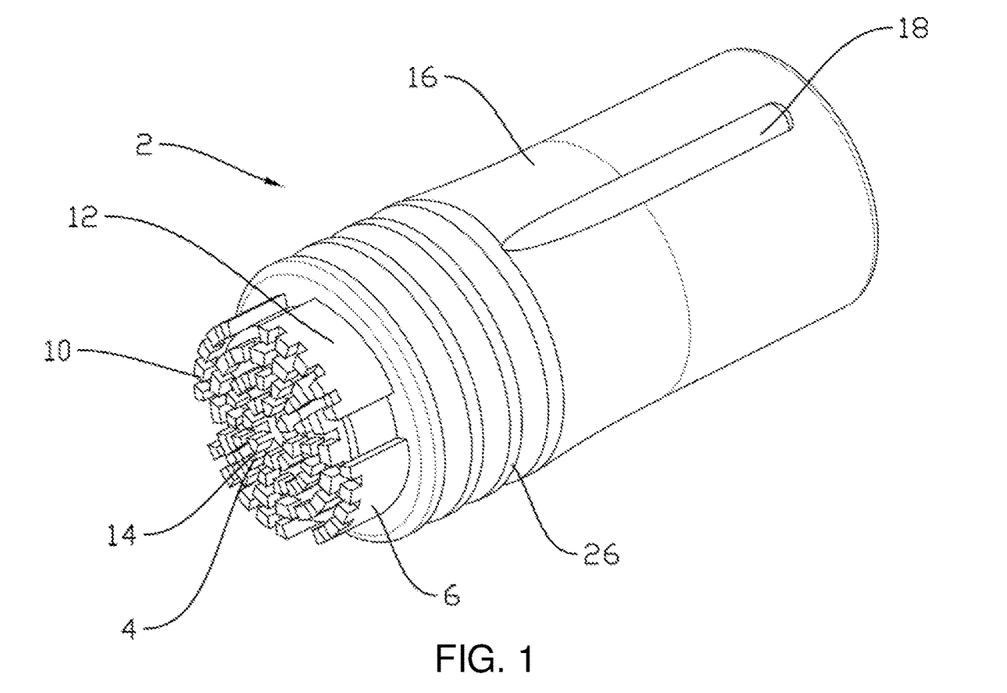
FIG. 1 is a perspective side elevation view of a sensor head, according to one implementation.

Turning to the FIGS, FIG. 1 through FIG. 8 illustrate one embodiment of parts of a multi-tip probe for obtaining bioelectrical measurements. FIG. 1 is a perspective view of a sensor head 2. As illustrated, a sensor head 2 having a casing 16, a sensor end 4, and a receiving cavity 24. The casing 16 may be formed of a plastic or other nonconducting material. The casing 16 may comprise a support structure 17 that may also be formed of a plastic or other nonconducting material and is used to support or holds in position the primary tip 14 and one or more ancillary tips, such as 6, 8, 10, 12. Located on the casing 16 are several raised ridges 26. The ridges 26 allow a user to grasp the sensor head 2. The ridges 26 may be made of the same material as the outer casing 16. However, to distinguish between different types of sensor heads 2, the ridges 26 may be made of different materials or have different colors. Located on the top of the sensor head 2 and on the outer circumference of the casing 16 is a rotational indicator 18. The rotational indicator 18 indicates to the user a top of the sensor head 2. The rotational indicator 18 assists the user in properly orientating and connecting the sensor head 2 to a probe 3 or a probe shaft 22. The rotational indictor 18 may be made of the same material as the outer casing 16.

The receiving cavity 24 is located on an opposite end of the from the sensor end 4 along a longitudinal axis of the sensor head 2. The receiving cavity 24 is sized to receive and couple to a probe shaft 22. A diameter and the length of the receiving cavity 24 is slightly larger than the probe shaft 22 such that when the sensor head 2 is attached to the probe 3 there is a secure connection that prevents the movement of the sensor head 2. In addition, the coupling of the sensor head 2 to the probe shaft 22 establishes electrical connection or communication between the sensor head 2 and a probe 3. The coupling between the sensor head 2 and the probe shaft 22 may provide a fit such that a deliberate force, e.g. by a user, is required to remove the sensor head 2. Those skilled in the art will recognize that different methods such as a friction fit, latch, or quick releasing mechanisms may secure the sensor head 2 to the probe 3.

Located on an edge of the receiving cavity 24 is a groove 28. The groove 28 corresponds with a tongue 30 or ridge located on the probe shaft 22. The groove 28 and tongue 30 assist the user in aligning the sensor head 2 to the probe 3 during attachment. In addition, the groove 28 and tongue 30 prevent the sensor head 2 from rotating when connected to the probe 3. The groove 28 and tongue 30 may cause electrical contacts between the sensor head 2 and probe shaft 22 to be aligned when the sensor head 2 is coupled to the probe 3.

The sensor end 4 has multiple sensor tips 5 including a primary conductive tip and a plurality of ancillary conductive tips. Other embodiments may include only a single ancillary tip (see e.g., FIG. 9). The primary conductive tip may include a center tip 14 and the plurality of ancillary conductive tips may include a first tip 6, a second tip 8, a third tip 10, and a fourth tip 12. The material of the sensor tips 5 may include brass, a brass alloy, brass plated metal, or other conductive material. The sensor tips 5 may be made of any material that will efficiently conduct an electrical signal. Each sensor tip 5 is independent and insulated from the other sensor tips such that each can take an independent conductance or other reading from the patient. While the figures show five independent sensor tips 5, one skilled in the art will recognize that anywhere from a total of two sensor tips or more may be used. At least one embodiment includes two tips including a primary conductive tip and an ancillary conductive tip. At least one embodiment includes more than two tips such as a primary conductive tip and more than one ancillary conductive tip. For example, one implementation includes a single primary conductive tip and four ancillary conductive tips. As another example, another implementation includes a single primary conductive tip and eight ancillary conductive tips. Any number of tips may be used. For example, the greater the number of ancillary conductive tips the more accurately it can be determined which direction has a higher conductivity because the tip(s) with the highest conductivity can be used as an indication of which direction the probe should be repositioned to in order to obtain a better (e.g., higher conductivity in at least some situations) measurement.

Each sensor tip 5 extends from the sensor end 4 to the receiving cavity 24. The length of the sensor tips 5 may extend far enough that the sensor tips 5 extend to a contact 20 located on the probe shaft 22. In some embodiments, a wire or conductor may run between a sensor tip to a contact within the receiving cavity 24 for providing electrical communication with a probe 3 or probe shaft 22. The casing 16 secures the sensor tips 5 to or within the sensor head 2.

Figure 2:
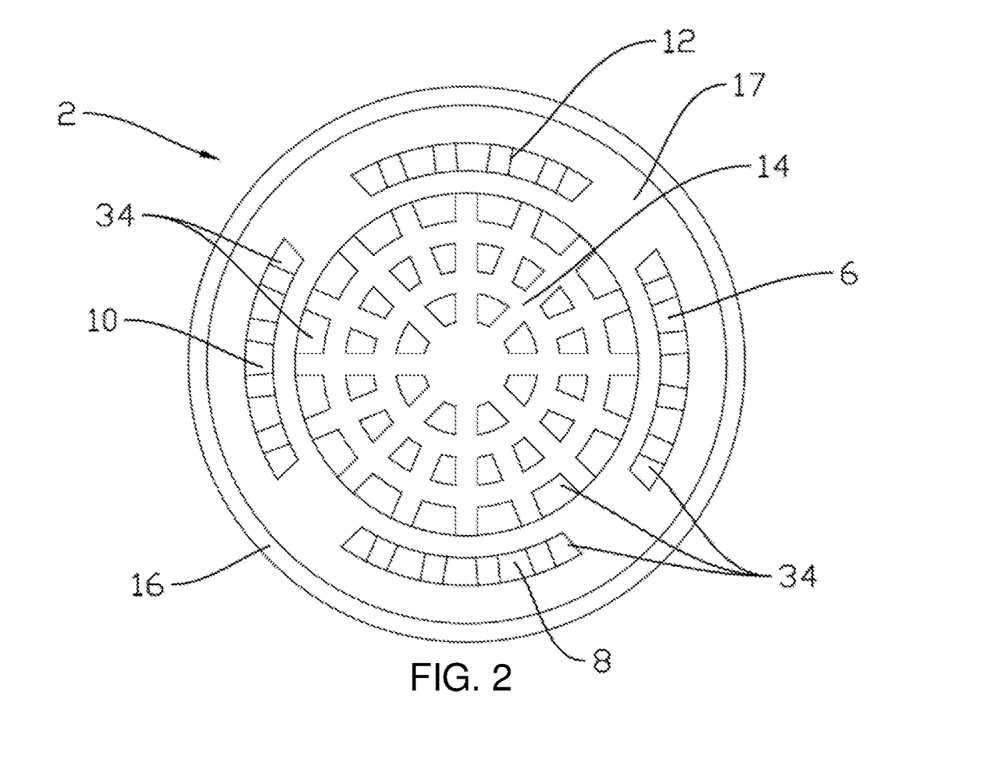
FIG. 2 is a front plan view of a sensor head showing a center tip and four ancillary tips, according to one implementation.
Figure 3:
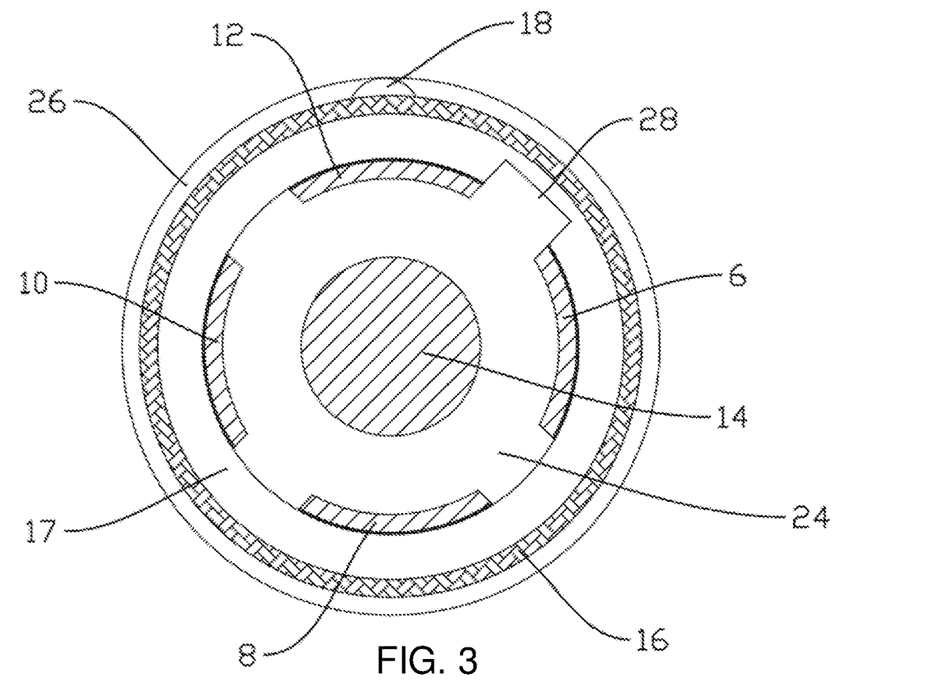
FIG. 3 is a cross-sectional view taken along the line A-A in FIG. 6 of the sensor head showing a receiving cavity and a groove, according to one implementation.

FIG. 2 is a front plan view of the sensor head 2 showing the location and organization of the sensor tips 5. FIG. 3 is a cross-sectional view taken along the line A-A of FIG. 6 of the sensor head 2 showing an interior of the receiving cavity 24. As shown in FIG. 2, a plurality of ancillary tips including a first tip 6, a second tip 8, a third tip 10, and a fourth tip 12 are substantially equally spaced around a perimeter of the center tip 14. While FIG. 2 shows that the first tip 6, second tip 8, third tip 10, and fourth tip 12 are arched in shape, generally any shape is acceptable. The center tip 14 and the ancillary tips may extend out from the outer casing 16 between 0.1 to 10 mm, in some embodiments.

A center tip 14 is located in the center of the sensor head 2. In the depicted embodiment, the center tip 14 has a round shape and approximately three-fourths to half the diameter as the sensor head 2. The center tip 14 extends from the sensor end 4 to the receiving cavity 24. A portion of the center tip 14 located in the receiving cavity 24 couples with a contact 32 located on the end of the probe shaft 22.

Each of the tips 5 have multiple bristles 34. While FIG. 2 shows a uniform bristle 34 pattern, the bristle 34 pattern may be random. The bristles 34 may be manufactured in any manner including using methods such as welding, etching molding, electrical discharge machining (EDM), machining, stamping, rotary broach, or any other manner. The bristles 34 puncture the cornified layer of the epidermis to assist in obtaining the bioelectric conductance value(s). The bristles allow the measurement to be taken closer to the conductance point without causing damage to the skin, cause pain, or even bleeding. In other embodiments, the bristles 34 do not puncture the cornified layer and may optionally be used in combination with a material, such as water or gels, to enhance obtaining the bioelectric conductance value(s).

As described above the sensor head 2 attaches to a probe 3. The probe 3 is any device that may be used to measure bioelectrical readings, such as readings at a meridian, acupressure point, or other conductance point. The probe 3 or a control unit sends the bioelectrical reading from to a computer or machine for storage, processing, display, or the like.

Figure 4:
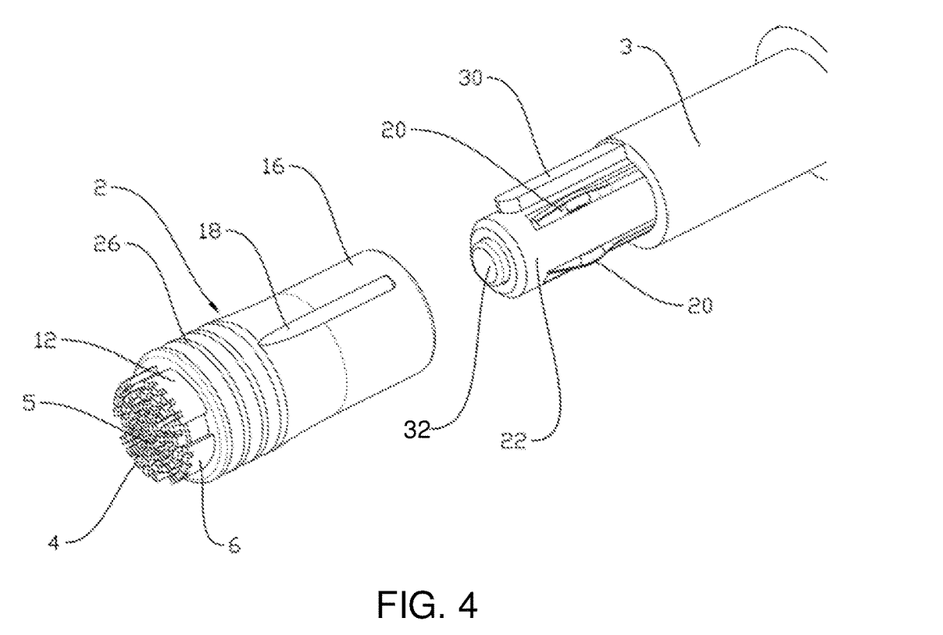
FIG. 4 illustrates a perspective side elevation view of the senor head and the probe removed from the sensor head, according to one implementation.
Figure 5:
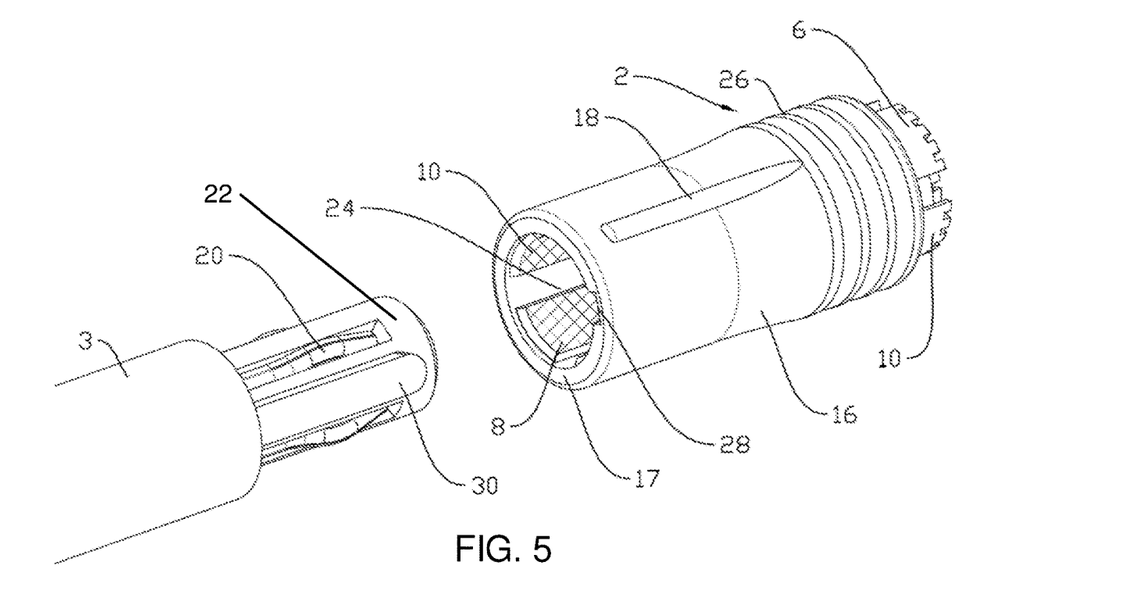
FIG. 5 is another perspective side elevation view of the senor head and the probe removed from the senor head, according to one implementation.
Figure 6:
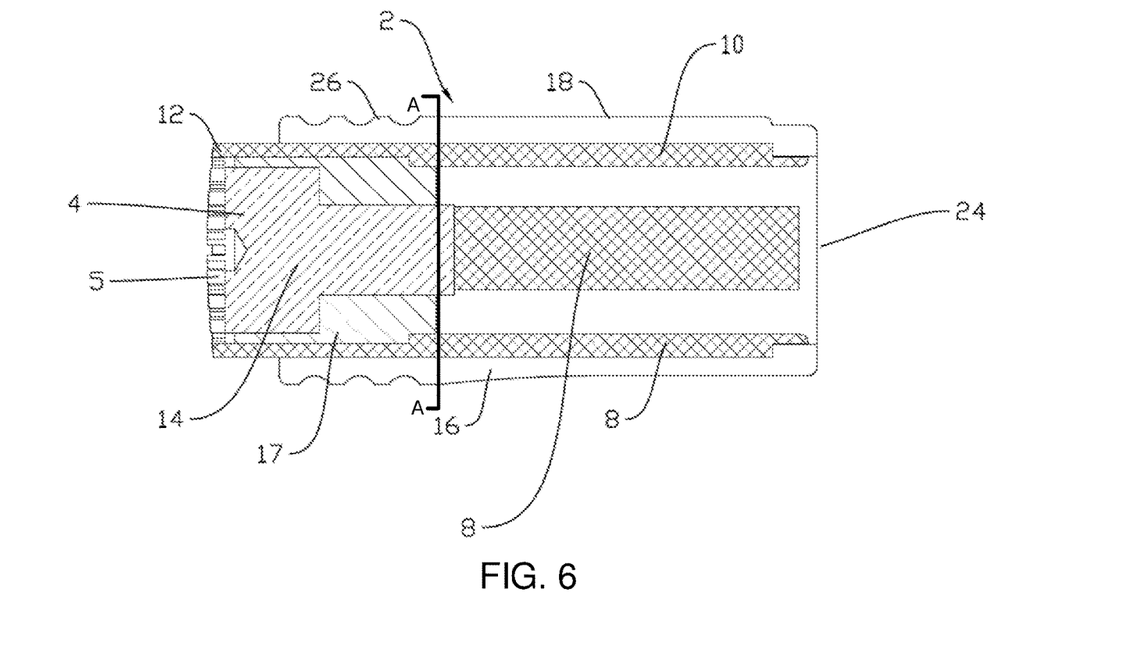
FIG. 6 is a cross-sectional side view of the sensor head illustrating the conductors corresponding to the sensor tips extending into the receiving cavity, according to one implementation.

FIG. 4 is a perspective view of the sensor head 2 and a portion of a probe 3 including a probe shaft 22. FIG. 5 is a perspective view of the sensor head 2 and portion of a probe 3 including a probe shaft 22 from a different view. FIG. 6 is a cross sectional side view illustrating arrangement of the tips and electrical contacts within the sensor head 2. As shown, a portion of the probe 3 that connects with the sensor head 2 is a probe shaft 22. Located on the probe shaft 22 are several contacts 20. Each contact 20 corresponds to a sensor tip 5. The contacts 20 may be used to measure the bioelectrical reading at the sensors tips 5 using the probe 3. In addition, the contacts 20 may apply pressure against the sensor head 2 (e.g., within an interior of the receiving cavity 24). This additional pressure assists in preventing the sensor head 2 from moving relative to the probe 3. The contacts 20 may be made of a conductive material such as brass, steel, or beryllium copper and the like.

Figure 7:
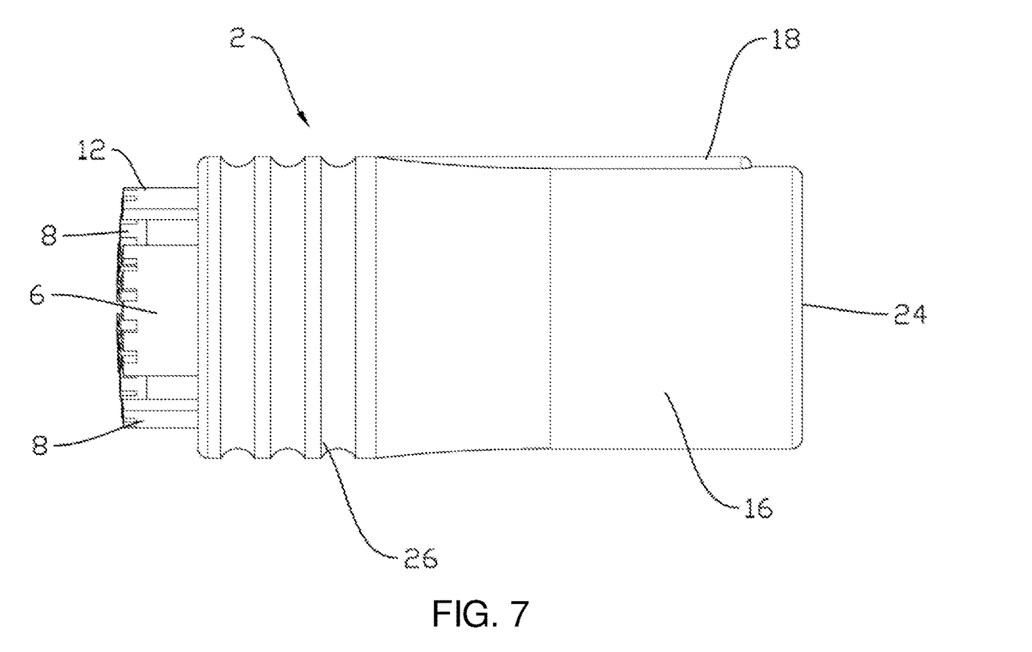
FIG. 7 is a side view of the sensor head, according to one implementation.
Figure 8:
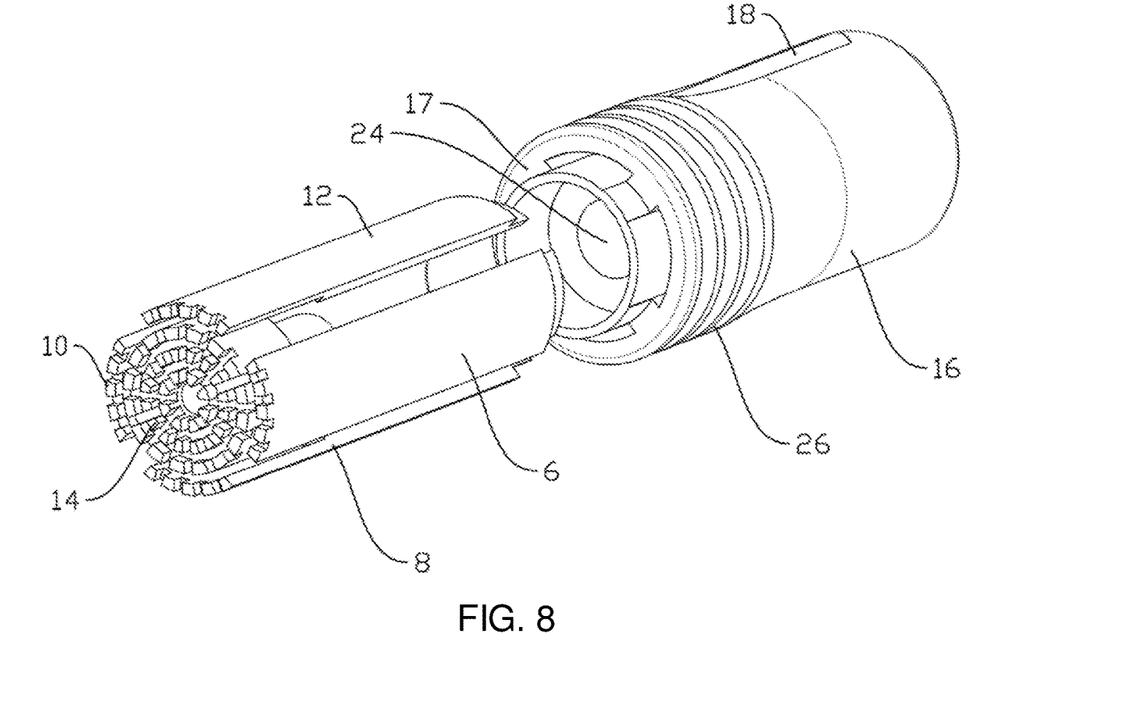
FIG. 8. illustrates a perspective view of a sensor head with the sensor tip conductors exploded from the sensor head, according to one implementation.

FIG. 7 is a side view of the sensor head 2. FIG. 8 is a perspective exploded view of the sensor head illustrating the shape of the sensor tips and the corresponding shape of the casing 16.

In operation, a user may obtain a probe 3 and a sensor head. The user may attach the sensor head 2 to the probe 3. The technician or user places the sensor head 2 on or near one of the conductance points (e.g., a bioelectric meridian or acupressure point) located on a dermal surface layer of a patient. The probe 3, or a probe controller, may obtain a bioelectric reading at each of the sensor tips 5. If the highest bioelectric reading is from the center tip 14 a reading is taken and recorded and the sensor head 2 may be removed from the patient's skin. If the highest bioelectric reading is from an ancillary tip (e.g., the first tip 6, the second tip 8, the third tip 10, or the fourth tip 12), the probe 3, controller, or other system may indicate to a user which sensor tip 5 has the highest bioelectric reading. The user may reposition the sensor head 2 on the dermal surface layer such that the center tip 14 has been moved to be located on or moved in the direction of the previous location of the sensor tip 5 that had the highest bioelectric reading. The sensor head 2 obtains another bioelectric reading. If the center tip 14 is now the highest bioelectric reading or shares the highest bioelectric reading along with one or more of the ancillary tips, the sensor head 2 is removed from the skin and the reading is recorded. If not, the sensor head 2 is readjusted toward the sensor tip 5 that has the highest conductance (or lowest impedance or resistance).

Figure 9:
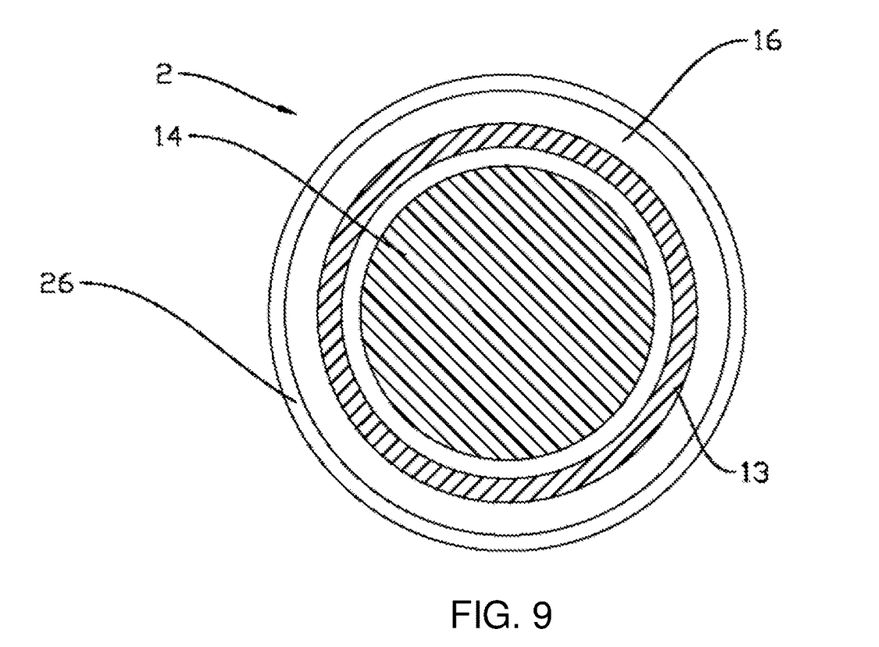
FIG. 9. is a front cross-sectional view of the sensor head showing a center tip with a single ancillary tip, according to one implementation.

FIG. 9 illustrates a front cross-sectional view of an end of a sensor head 2 having two conductive tips, according to one embodiment. Specifically, the sensor head includes a center tip 14 and an ancillary tip 13 encircling the center tip 14. The arrangement of tips may be used to determine whether the center tip 14 is positioned over a conductance point. For example, if the ancillary tip 13 has a higher conductance reading (i.e., lower resistance or impedance) it can be determined that the conductance point is probably not located under the center tip 14 and that the sensor head 2 should be repositioned. However, the two-tip configuration in FIG. 9 may not be helpful in determining a direction of the conductance point. For example, a five-tip configuration as illustrated in FIGS. 1-8 may be used to determine a direction where the conductance point is likely located based on determining the ancillary tip that has the highest conductance reading.

Figure 10:
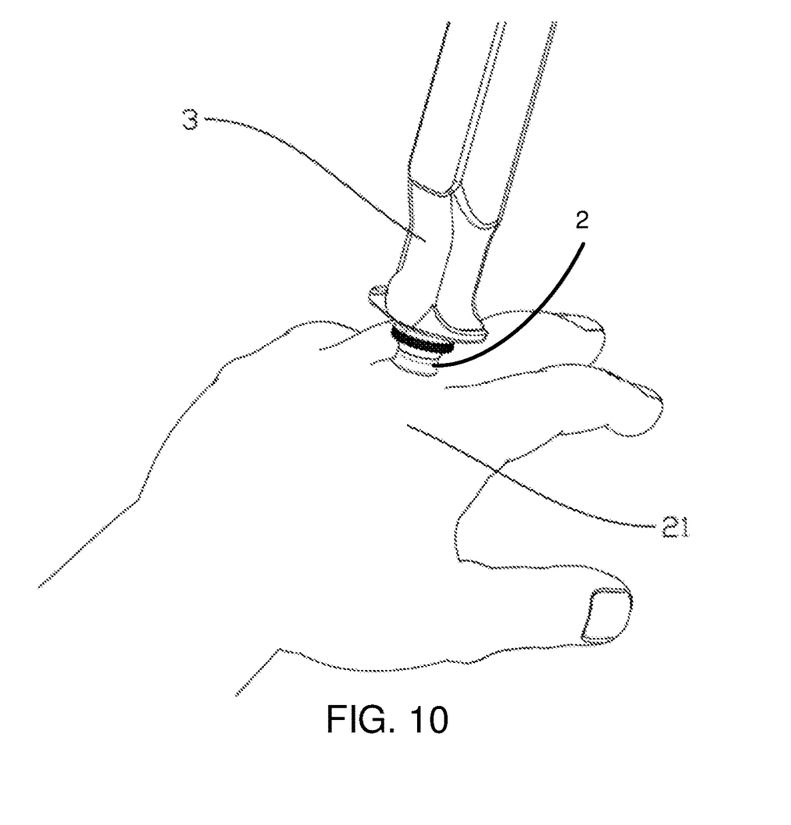
FIG. 10. is a perspective view of a probe contacting a dermal surface layer of a patient to obtain bioelectrical reading, according to one implementation.

FIG. 10 is a perspective view illustrating a probe 3 being positioned on a dermal layer 21 of a patient's hand. The probe 3 includes a handle attached to the sensor head 2. The handle of the probe 3 allows a user to hold, position, and provide pressure to contact the dermal layer 21 with ay tips of the sensor head 2 so that a bioelectrical reading can be obtained.

Figure 11:
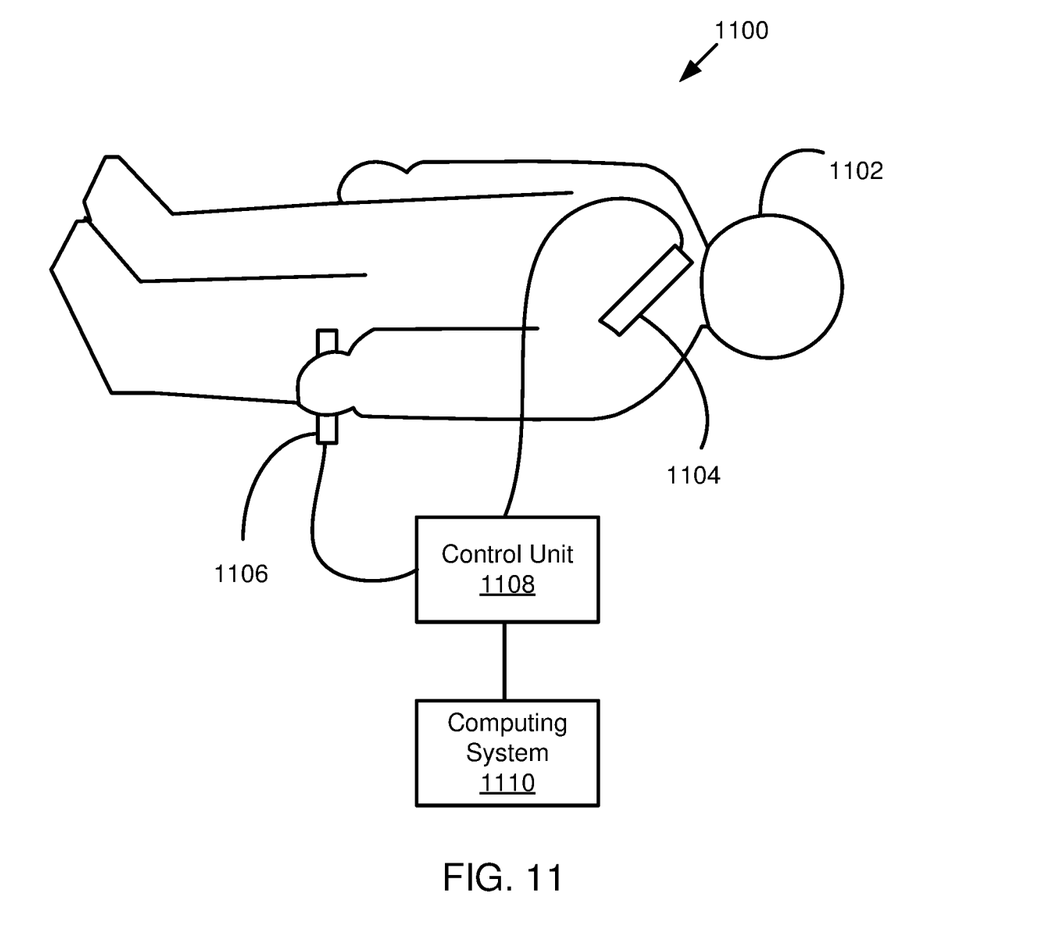
FIG. 11 is a schematic block diagram illustrating a system for obtaining bioelectric measurements from a patient, according to one implementation.

FIG. 11 is a schematic block diagram illustrating a system 1100 for obtaining bioelectric measurements from a patient 1102, according to one embodiment. The system 1100 includes a probe 1104, a ground contact 1106, a control unit 1108, and a computing system 1110.

The probe 1104 may include a probe and sensor head such as the probe 3 or head probe 2 in any of FIGS. 1-10. For example, the probe 1104 may include a sensor head having a plurality of conductive tips including a primary conductive tip and an ancillary (or secondary) conductive tip. The ground contact 1104 may include a conductive rod or other device having a conductive surface for grounding a portion of the body of the patient 1102. The ground contact 1106 and the probe 1104 are connected to the control unit 1104 via cables or other conductors. In one embodiment, the control unit 1108 may be included within the probe 1104, such as within a handle or body of the probe 1104.

Figure 13:
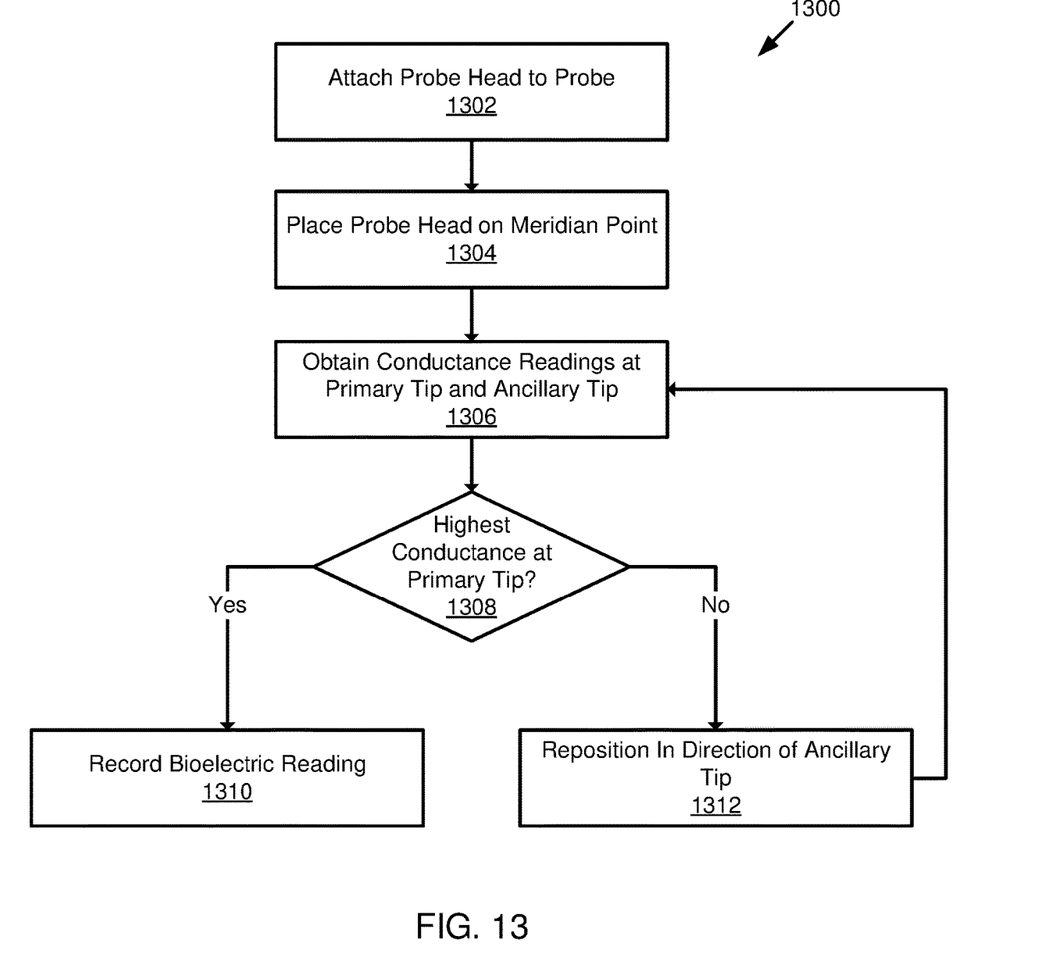
FIG. 13 is a schematic flow chart diagram illustrating a method for obtaining bioelectric readings from a patient, according to one implementation.
Figure 14:
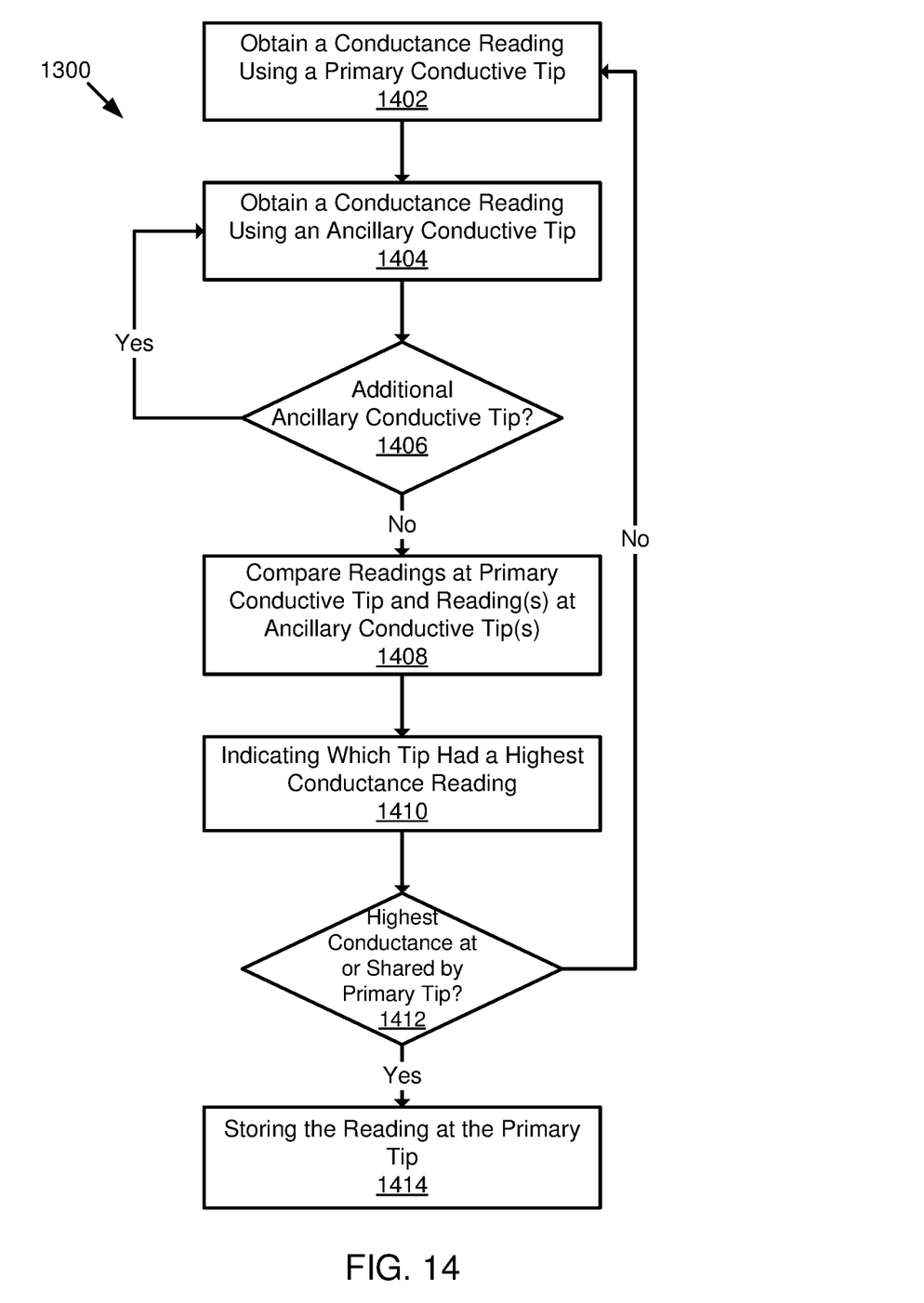
FIG. 14 is a schematic flow chart diagram illustrating a method for obtaining bioelectric readings from a patient, according to another implementation.

The control unit 1108 obtains measurements of conductivity or other bioelectrical measurements using the probe 1104 and the ground contact 1106. For example, the control unit 1108 may provide a voltage or other signal and measure a resistance, conductance, or other measurement of a load between one or more tips of the probe 1104 and the ground contact 1106. For example, a user or practitioner may have a patient hold the ground contact 1106 and then place the probe 1104 at a desired conductance location or other measurement point. Upon positioning the probe 1104, the user or practitioner may press a button or otherwise provide input to the control unit 1108 or probe 1104 to begin a measurement process. The control unit 1108 may perform a measurement process at each of the contact tips (e.g., a primary tip and an ancillary tip). For example, the control unit 1108 may provide power and measure a resistance or conductance between the probe 1104 and the ground contact as illustrated in FIGS. 13 and/or 14. If the primary tip has the highest conductance (or lowest resistance) the control unit 1108 may send the measurement at the primary tip to the computing system 1110 for display or storage. If the primary tip does not have the highest conductance (or lowest resistance) the control unit 1108 may indicate to a user or practitioner via an interface or the computing system 1110 that a new reading should be obtained. The user or practitioner may reposition the probe 1104 and take another reading.

The control unit 1108 may include a processor, computer readable memory, a power supply, a circuit for measuring resistance or conductance, or other circuitry or hardware for measuring or storing bioelectric readings. The processor may include a low power processor and the computer readable memory may store instructions that cause the processor to control the control unit 1108, including its circuitry to obtain bioelectric readings using the ground surface may include a processor and memory for controlling a power supply, measuring electrical characteristics between a probe tip and ground contacts, or the like.

Figure 12A:
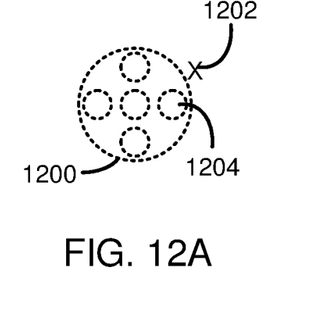
FIGS. 12A, 12B, and 12C illustrate sequential positioning of a sensor head with respect to a conductance point to obtain a reading at the conductance point, according to one implementation.
Figure 12B:
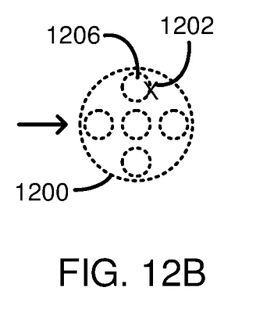
Figure 12C:
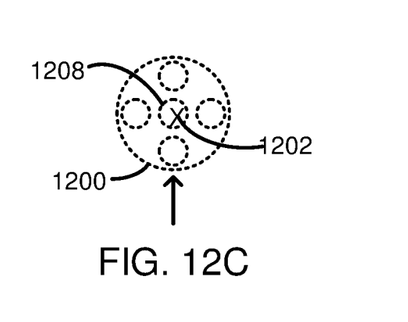

FIGS. 12A, 12B, and 12C illustrate sequential positioning of a sensor head 1200 with respect to a conductance point 1202 to obtain a reading at the conductance point 1202. FIG. 12A illustrates the sensor head 1200 at a first location with respect to the conductance point 1202. A reading at the first location results in a highest conductance being measured at a first ancillary tip 1204. Based on the conductance being highest at the first ancillary tip 1204 the user may reposition the sensor head 1200 to the right at a second location, as shown in FIG. 12B. A reading at the second location may be obtained. Because a second ancillary tip is closest to the conductance point 1202, the highest conductance may be measured by a second ancillary tip 1206. Based on the conductance being highest at the second ancillary tip 1206 the user may reposition the sensor head 1200 upward at a third location, as shown in FIG. 12C. A reading at the third location may be obtained. Because a primary tip is closest to and overlaps the conductance point 1202, the highest conductance may be measured by the primary tip 1208. Because the highest conductance reading is found at the primary tip 1208, it can be determined that the sensor head is properly positioned over the conductance reading and the reading at the primary tip 1208 can be logged or stored.

FIG. 13 is a schematic flow chart diagram illustrating an example method 1300 for obtaining bioelectric readings from a patient. The method 1300 may be performed by a user or practitioner and a multi-tip sensor head, such as the multi-tip sensor head in any of FIGS. 1-12.

The method 1300 begins and a user attaches 1302 a sensor head to a probe. For example, the user may attach 1302 a sensor head or the sensor head 2 of FIGS. 1-8 to the probe shaft 22 and/or probe 3 of FIG. 4, 5, or 10. The user places 1304 the sensor head at a meridian point. The meridian point may include a bioelectric measurement point, acupuncture point, conductance point, or any other location on the patient's skin or body. The user may provide a sufficient amount of pressure to hold the probe tip against the patient's skin. The user obtains 1306 conductance readings at a primary tip and an ancillary tip of the sensor head. For example, the user may obtain 1306 the conductance readings by pressing a button on the probe or a control unit to cause the probe or control unit to obtain conductance readings at each conductive tip of the sensor head.

In one embodiment, the probe or control unit determines 1308 whether the highest conductance was at the primary tip of the sensor head. If so (Yes at 1308), the control unit, a computing system, or the user records 1310 the bioelectric reading found at the primary tip. If not (No at 1308), the user repositions 1312 the sensor head in direction of an ancillary tip that had the highest conductance reading. For example, if an ancillary tip positioned to the right of the primary tip had a highest conductance, the user would reposition 1312 the sensor head to the right. The user may then obtain 1306 conductance readings at the primary tip and the ancillary tip(s). The obtaining 1306, determining 1308, and repositioning 1312 may be performed repeatedly until the primary tip has the highest conductance reading (Yes at 1308).

FIG. 14 is a schematic flow chart diagram illustrating an example method 1400 for obtaining bioelectric readings from a patient. The method 1400 may be performed by a probe having a multi-tip sensor head or a control unit for a multi-tip sensor head, such as the probe 3 and/or sensor head 2 in any of FIGS. 1-10 or the probe 1104 and/or control unit 1108 of FIG. 11.

The method 1400 begins and a control unit 1108 obtains 1402 a conductance reading using a primary conductive tip. For example, the control unit 1108 may cause power from a power supply to be provided to the primary conductive tip and measure the voltage drop between the primary conductive tip and a grounding contact to obtain a resistance or conductance reading. The control unit 1108 obtains 1404 a conductance reading using an ancillary conductive tip. For example, the control unit 1108 may cause power from a power supply to be provided to the ancillary conductive tip and measure the voltage drop between the ancillary conductive tip and a grounding contact to obtain a resistance or conductance reading. Because the ancillary conductive tip is electrically isolated from the primary conductive tip, the measurement at the ancillary conductive tip may be an independent measurement of conductance. The control unit 1108 may determine 1406 whether there are any additional conductive tips. If there is an additional ancillary conductive tip (Yes at 1406), the control unit 1108 obtains 1404 a conductance reading at the additional ancillary conductive tip. If there is no additional ancillary conductive tip (No at 1406), the control unit 1108 compares 1408 the readings for the primary conductive tip and any ancillary conductive tips. The control unit 1108 may indicate 1410 which tip had the highest conductance reading. For example, the control unit 1108 may indicate 1410 activating an indicator light or speaker, or by forwarding information to a computing device or display to provide the indication to a user.

The control unit 1108 determines 1412 whether the highest conductance was found at the primary conductive tip or whether the highest conductance was shared among the primary tip and one or more of the ancillary tips. If the primary conductive tip had or shared the highest conductance (Yes at 1412), the control unit 1108 stores 1414 the reading at the primary tip at the measurement. The control unit 1108 may store 1414 the reading by storing in memory or forwarded to a computing device for storage and/or processing. If the primary conductive tip does not have or share the highest conductance (No at 1412), the control unit 1108 may wait for a user to reposition the probe and begin again at obtaining 1402 a conductance reading for a primary tip. In an embodiment, the method includes indicating which ancillary tip had the greatest conductance reading and then indicating that the primary tip should be repositioned where the ancillary tip having the greatest reading was located. The method 1400 may be repeated until the primary conductive tip has the highest conductance reading or shares the highest conductance reading with one or more of the ancillary tips.

Figure 15:
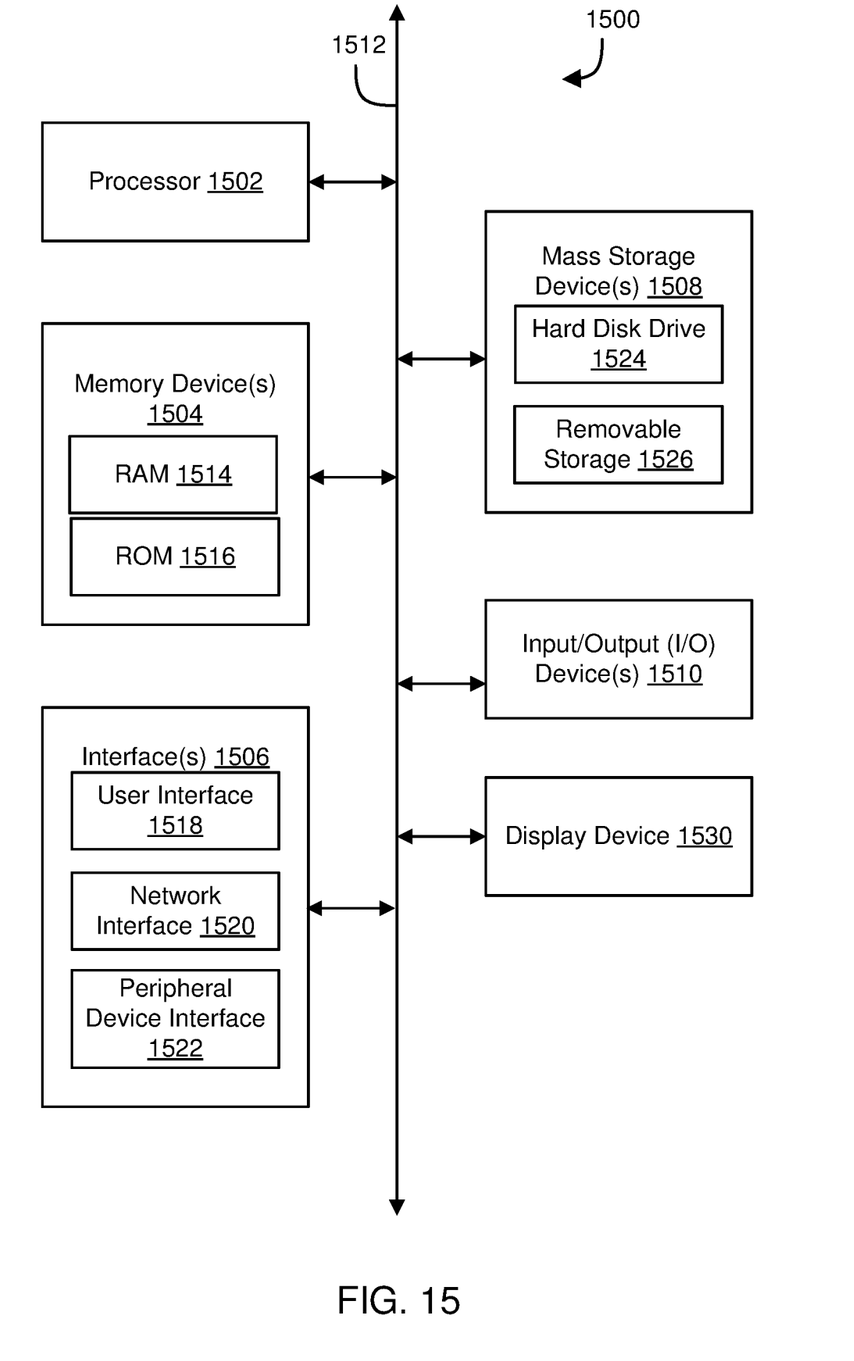
FIG. 15 is a schematic block diagram illustrating a computing device, according to one implementation.

Referring now to FIG. 15, a block diagram of an example computing device 1500 is illustrated. Computing device 1500 may be used to perform various procedures, such as those discussed herein. In one embodiment, the computing device 1500 can function as a computing system 1110, control unit 1108, or the like. Computing device 1500 can perform various monitoring functions as discussed herein, and can execute one or more application programs, such as the application programs or functionality described herein. Computing device 1500 can be any of a wide variety of computing devices, such as a microprocessor, desktop computer, in-dash computer, vehicle control system, a notebook computer, a server computer, a handheld computer, tablet computer and the like.

Computing device 1500 includes one or more processor(s) 1502, one or more memory device(s) 1504, one or more interface(s) 1506, one or more mass storage device(s) 1508, one or more Input/Output (I/O) device(s) 1510, and a display device 1530 all of which are coupled to a bus 1512. Processor(s) 1502 include one or more processors or controllers that execute instructions stored in memory device(s) 1504 and/or mass storage device(s) 1508. Processor(s) 1502 may also include various types of computer-readable media, such as cache memory.

Memory device(s) 1504 include various computer-readable media, such as volatile memory (e.g., random access memory (RAM) 1514) and/or nonvolatile memory (e.g., read-only memory (ROM) 1516). Memory device(s) 1504 may also include rewritable ROM, such as Flash memory.

Mass storage device(s) 1508 include various computer readable media, such as magnetic tapes, magnetic disks, optical disks, solid-state memory (e.g., Flash memory), and so forth. As shown in FIG. 15, a particular mass storage device is a hard disk drive 1524. Various drives may also be included in mass storage device(s) 1508 to enable reading from and/or writing to the various computer readable media. Mass storage device(s) 1508 include removable media 1526 and/or non-removable media.

I/O device(s) 1510 include various devices that allow data and/or other information to be input to or retrieved from computing device 1500. Example I/O device(s) 1510 include cursor control devices, keyboards, keypads, microphones, monitors or other display devices, speakers, printers, network interface cards, modems, and the like.

Display device 1530 includes any type of device capable of displaying information to one or more users of computing device 1500. Examples of display device 1530 include a monitor, display terminal, video projection device, and the like.

Interface(s) 1506 include various interfaces that allow computing device 1500 to interact with other systems, devices, or computing environments. Example interface(s) 1506 may include any number of different network interfaces 1520, such as interfaces to local area networks (LANs), wide area networks (WANs), wireless networks, and the Internet. Other interface(s) include user interface 1518 and peripheral device interface 1522. The interface(s) 1506 may also include one or more user interface elements 1518. The interface(s) 1506 may also include one or more peripheral interfaces such as interfaces for printers, pointing devices (mice, track pad, or any suitable user interface now known to those of ordinary skill in the field, or later discovered), keyboards, and the like.

Bus 1512 allows processor(s) 1502, memory device(s) 1504, interface(s) 1506, mass storage device(s) 1508, and I/O device(s) 1510 to communicate with one another, as well as other devices or components coupled to bus 1512. Bus 1512 represents one or more of several types of bus structures, such as a system bus, PCI bus, IEEE bus, USB bus, and so forth.

For purposes of illustration, programs and other executable program components are shown herein as discrete blocks, although it is understood that such programs and components may reside at various times in different storage components of computing device 1500, and are executed by processor(s) 1502. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

EXAMPLES

The following examples pertain to further embodiments.

Example 1 is a device for obtaining an electrical conductance reading from a patient. The device includes a sensor head for contacting a patient's skin. The device includes a primary conductive tip positioned on the sensor head. The device includes an ancillary conductive tip positioned on the sensor head to contact a different portion of the patient's skin than the primary conductive tip. The primary conductive tip and the ancillary conductive tip are electrically isolated from each other. The primary conductive tip and the ancillary conductive tip are configured to contact a patient's skin when the sensor head is placed against the patient's skin to obtain independent measurements of electrical conductance.

In Example 2, the device of Example 1 further includes one or more additional ancillary conductive tips positioned on the sensor head.

In Example 3, the ancillary conductive tip and the one or more additional ancillary conductive tips in any Example 2 are positioned laterally around the primary conductive tip.

In Example 4, the primary conductive tip in any of Examples 2-3 is positioned substantially at a center of the sensor head and the ancillary conductive tip and the one or more additional ancillary conductive tips are positioned around a perimeter of the primary conductive tip.

In Example 5, the sensor head in any of Examples 1-4 includes a sensor end and a receiving cavity for receiving a probe shaft mechanically coupled to a probe handle.

In Example 6, the sensor head of Example 5 is selectively removable from the probe shaft.

In Example 7, the sensor head of any of Examples 5-6 further includes a plurality of electrical contacts for providing electrical communication between the primary conductive tip and the ancillary conductive tip to conductors on the probe shaft or probe handle.

In Example 8, each of the primary conductive tip and the ancillary conductive tip of any of Examples 1-7 extend from a surface of the sensor head to provide isolated electrical contact with the patient's skin.

In Example 9, an interior surface of the receiving cavity of any of Examples 1-8 forms a groove. The probe shaft includes a ridge corresponding to the groove for aligning the sensor head with the probe shaft. The ridge and the groove prevent the rotational movement of the sensor head with respect to the probe shaft.

Example 10 is a method for positioning a probe to obtain an electrical conductance reading from a patient. The method includes obtaining a first conductance reading using a primary conductive tip positioned on a sensor head. The method includes obtaining a second conductance reading using an ancillary conductive tip positioned on the sensor head laterally from the primary conductive tip. The method includes comparing the first measurement to the second measurement. The method further includes indicating to a user whether the primary conductive tip or the ancillary conductive tip had a higher conductance.

In Example 11, the method of Example 10 further includes storing the first conductance reading as a conductance measurement if the primary tip had a highest conductance reading.

In Example 12, The method of any of Examples 10-11 further includes obtaining conductance readings for one or more additional ancillary conductive tips. Indicating whether the primary conductive tip or the ancillary conductive tip has a higher conductance reading includes indicating which of the primary conductive tip and the ancillary conductive tip has the highest conductance reading.

In Example 13, indicating to the user whether the primary conductive tip or the ancillary conductive tip has the higher conductance reading in any of Examples 10-12 includes one or more of: activating an indicator light; providing an indication on a display or directional indicator; and playing an audible sound indicating that the primary conductive tip did or did not have the higher conductance reading.

In Example 14, the method of any of Examples 10-13 further includes providing a probe, the probe comprising: a sensor head for contacting the patient's skin; the primary conductive tip positioned on the sensor head; and the ancillary conductive tip positioned on the sensor head to contact a different portion of the patient's skin than the primary conductive tip. The primary conductive tip and the ancillary conductive tip are electrically isolated from each other, and the primary conductive tip and the ancillary conductive tip are configured to contact a patient's skin when the sensor head is placed against the patient's skin to obtain independent measurements of electrical conductance.

In Example 15, the method of Example 14 further includes placing the sensor head on a probe shaft, the probe shaft in mechanical communication with a probe handle.

In Example 16, the method of Example 15 further includes positioning the sensor head against skin of a patient such shat the primary conductive tip and the ancillary conductive tip contact a dermal layer of the skin.

In Example 17, the method of any of Examples 10-16 further includes repositioning the sensor head in the direction of the ancillary conductive tip if the second conductance reading is higher than the first conductance reading.

In Example 18, the method of any of Examples 10-17 further includes repeating obtaining conductance readings at a new location on the skin if the primary conductive tip does not have the highest conductivity reading.

Example 19 is a system for obtaining electrical conductance reading from a patient. The system includes a probe having a probe handle and a sensor head. The sensor head is for contacting a patient's skin and includes a primary conductive tip positioned on the sensor head and an ancillary conductive tip positioned on the sensor head to contact a different portion of the patient's skin than the primary conductive tip. The primary conductive tip and the ancillary conductive tip are electrically isolated from each other. The primary conductive tip and the ancillary conductive tip are configured to contact a patient's skin when the sensor head is placed against the patient's skin to obtain independent measurements of electrical conductance. The system further includes a grounding contact for grounding a location on the patient's body and a control unit for measuring conductance between the primary conductive tip and the grounding contact and between the ancillary conducting tip and the grounding contact.

In Example 20, a measurement between the primary conductive tip and the grounding contact of Example 19 includes a first reading and a measurement between the ancillary conducting tip and the grounding contact includes a second reading. The control unit is further configured to compare the first reading to the second reading and indicate to a user whether the primary conductive tip or the ancillary conductive tip had a higher conductance or indicate whether the primary conductive tip or the ancillary conductive tip had the same conductance.

In Example 21, a measurement between the primary conductive tip and the grounding contact of Example 19 includes a first reading and a measurement between the ancillary conducting tip and the grounding contact includes a second reading. The control unit is further configured to compare the first reading to the second reading and indicate to a user whether the primary conductive tip or the ancillary conductive tip had a higher conductance or whether one or more of the primary conductive tip and the ancillary conductive tips have the same or similar reading.

In Example 22, the control unit of Example 20 or 21 is further configured to store the first reading as a conductance measurement if the primary conductive tip had a highest conductance.

In Example 23, the sensor head in any of Examples 20-22 further includes a plurality of additional ancillary conductive tips, wherein the control unit is further configured to obtain conductance readings for the one or more additional ancillary conductive tips. Indicating whether the primary conductive tip or the one or more ancillary conductive tips has a higher conductance reading includes indicating which of the tips had the highest conductance reading.

In Example 24, the system of any of Examples 20-23 further includes one or more of an indicator light, a display, or a speaker. Indicating to the user whether the primary conductive tip or the ancillary conductive tip had the higher conductance reading includes one or more of: activating the indicator light in a predetermined manner; providing an indication on the display; or playing an audible sound using the speaker indicating that the primary conductive tip did or did not have the higher conductance reading.

Example 25 is an apparatus including means to perform a method or realize a system as in of any of Examples 1-24.

Example 26 is a machine readable storage including machine-readable instructions, when executed, to implement a method or realize an apparatus or system of any of Examples 1-25.

Various techniques, or certain aspects or portions thereof, may take the form of program code (i.e., instructions) embodied in tangible media, such as floppy diskettes, CD-ROMs, hard drives, a non-transitory computer readable storage medium, or any other machine readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network. The components may be passive or active, including agents operable to perform desired functions.

Reference throughout this specification to "an example" means that a particular feature, structure, or characteristic described in connection with the example is included in at least one embodiment of the present disclosure. Thus, appearances of the phrase "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present disclosure may be referred to herein along with alternatives for the various components thereof. It is understood that such embodiments, examples, and alternatives are not to be construed as de facto equivalents of one another, but are to be considered as separate and autonomous representations of the present disclosure.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered illustrative and not restrictive.

Those having skill in the art will appreciate that many changes may be made to the details of the above-described embodiments without departing from the underlying principles of the disclosure. The scope of the present disclosure should, therefore, be determined only by the following claims.

What is claimed is:

1. A device for obtaining an electrical conductance reading from a bioelectric meridian point of a patient, the device comprising:
    a sensor head configured to contact a patient's skin at a first location;
    a primary conductive tip positioned on the sensor head; and
    an ancillary conductive tip positioned on the sensor head configured to contact a different portion of the patient's skin than the primary conductive tip;
    wherein the primary conductive tip and the ancillary conductive tip are configured to contact the patient's skin when the sensor head is placed against the patient's skin;
    wherein the primary conductive tip and the ancillary conductive tip are electrically isolated from each other to obtain independent measurements of electrical conductance when the sensor head is placed against the patient's skin;
    wherein the device obtains a primary electrical conductance reading between the primary conductive tip and a grounding contact configured to contact the patient's skin at a second location; and
    wherein the device obtains at least one ancillary electrical conductance reading between the ancillary conductive tip and the grounding contact.

2. The device of claim 1, further comprising one or more additional ancillary conductive tips positioned on the sensor head.

3. The device of claim 2, wherein the ancillary conductive tip and the one or more additional ancillary conductive tips are positioned laterally around the primary conductive tip.

4. The device of claim 2, wherein the primary conductive tip is positioned substantially at a center of the sensor head and the ancillary conductive tip and the one or more additional ancillary conductive tips are positioned around a perimeter of the primary conductive tip.

5. The device of claim 1, wherein the sensor head comprises a sensor end and a receiving cavity for receiving a probe shaft mechanically coupled to a probe handle.

6. The device of claim 5, wherein the sensor head is selectively removable from the probe shaft.

7. The device of claim 5, the sensor head further comprising a plurality of electrical contacts for providing electrical communication between the primary conductive tip and the ancillary conductive tip to conductors on the probe shaft or probe handle.

8. The device of claim 1, wherein each of the primary conductive tip and the ancillary conductive tip extend from a surface of the sensor head to provide isolated electrical contact with the patient's skin.

9. The device of claim 5 wherein an interior surface of the receiving cavity forms a groove, wherein the probe shaft comprises a ridge corresponding to the groove for aligning the sensor head with the probe shaft, and wherein the ridge and the groove prevent the rotational movement of the sensor head with respect to the probe shaft.

10. The device of claim 1, wherein the primary conductive tip and the ancillary conductive tip are configured to contact the patient's skin and obtain the independent measurements of electrical conductance without puncturing the patient's skin.

11. The device of claim 1, wherein the primary conductive tip is positioned substantially at a center of the sensor head and the ancillary conductive tip and one or more additional ancillary conductive tips are positioned around a perimeter of the primary conductive tip.

12. The device of claim 11, wherein the ancillary conductive tip and the one or more additional ancillary conductive tips are each shaped as an arc adjacent to the primary conductive tip.

13. The device of claim 1, wherein the primary conductive tip is positioned substantially at a center of the sensor head and the ancillary conductive tip is a continuous ring encircling the primary conductive tip.

* * * * *